United States Patent
Dixon et al.

(10) Patent No.: US 7,104,991 B2
(45) Date of Patent: *Sep. 12, 2006

(54) METHOD AND DEVICE FOR USING EXTENDED INTERFERENCE FIT SCREW SHANKS FOR SPINAL STABILIZATION

(76) Inventors: Robert A Dixon, 10577 Durham Pl., Powell, OH (US) 43065; Donald J. Hackman, 3499 Kirkham Rd., Columbus, OH (US) 43221

( * ) Notice: Subject to any disclaimer, the term of this patent is extended or adjusted under 35 U.S.C. 154(b) by 181 days.

This patent is subject to a terminal disclaimer.

(21) Appl. No.: 10/083,332

(22) Filed: Feb. 25, 2002

(65) Prior Publication Data

US 2002/0120271 A1 Aug. 29, 2002

Related U.S. Application Data

(60) Provisional application No. 60/271,782, filed on Feb. 27, 2001.

(51) Int. Cl.
*A61B 17/70* (2006.01)

(52) U.S. Cl. .............................. 606/61; 606/69; 606/73

(58) Field of Classification Search ................. 606/61, 606/69, 70, 71, 73
See application file for complete search history.

(56) References Cited

U.S. PATENT DOCUMENTS

| | | | |
|---|---|---|---|
| 4,488,543 A * | 12/1984 | Tornier | 606/65 |
| 5,275,601 A | 1/1994 | Gogolewski et al. | |
| 5,360,452 A * | 11/1994 | Engelhardt et al. | 623/22.37 |
| 5,681,311 A * | 10/1997 | Foley et al. | 606/61 |
| 5,904,684 A * | 5/1999 | Rooks | 606/69 |
| 5,954,722 A * | 9/1999 | Bono | 606/61 |
| 6,030,389 A * | 2/2000 | Wagner et al. | 606/71 |
| 6,197,028 B1 | 3/2001 | Ray et al. | |
| 6,228,085 B1 * | 5/2001 | Theken et al. | 606/61 |
| 6,306,136 B1 | 10/2001 | Baccelli | |
| 6,605,090 B1 * | 8/2003 | Trieu et al. | 606/69 |
| 6,656,181 B1 * | 12/2003 | Dixon et al. | 606/69 |

* cited by examiner

*Primary Examiner*—David O. Reip
(74) *Attorney, Agent, or Firm*—Standley Law Group LLP

(57) ABSTRACT

A device and a method for stabilizing vertebrae in a human spine for the purpose of fixing one vertebra with respect to other vertebrae and with respect to other parts of the spinal column. This device comprises bone screws that clamp to a plate to maintain the plate in contact with the vertebrae. The device may be fabricated from non-metals, metal, alloys, or composite materials. A tapered screw head is pulled into the plate with the taper extending through the plate into the underlying bone. Extending the taper into the bone moves the screw thread stress raiser into an area of lesser deflection. This strengthens the fixation by increasing the rigidity and reducing the risk of screw breakage. Extending the taper into the underlying bone has also been shown to strengthen the taper lock.

5 Claims, 3 Drawing Sheets

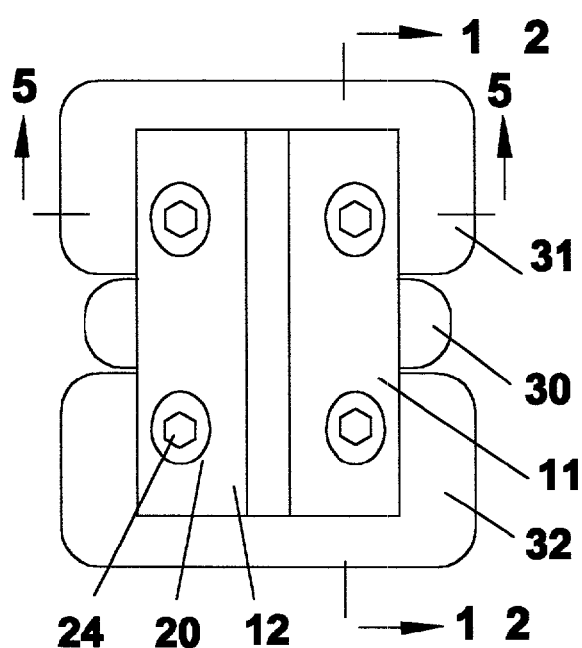
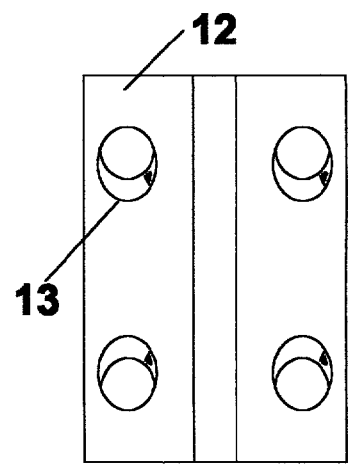
FIG. 3
FIG. 4
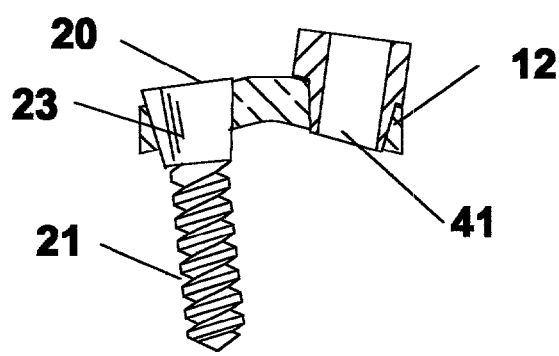
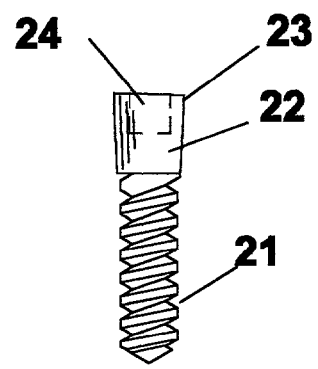
FIG. 5
FIG. 6

METHOD AND DEVICE FOR USING EXTENDED INTERFERENCE FIT SCREW SHANKS FOR SPINAL STABILIZATION

CROSS-REFERENCES TO RELATED APPLICATIONS

This patent claims the benefit of U.S. provisional application Ser. No. 60/271,782 filed Feb. 27, 2001.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

This invention relates generally to implantable medical devices and their methods of use for stabilizing skeletal bone, and relates more particularly to fasteners for attaching implantable medical devices and their use for stabilizing the vertebrae of a human spine.

With normal anatomy, the vertebrae of the spinal column are held together and to the skeleton by a complex arrangement of ligaments, tendons and muscles. Degenerative diseases, deformities, or trauma may cause abnormal conditions. These problems generally cause or allow displacement or rotation of a vertebra relative to the adjacent vertebrae, or produce painful motion. When spinal discs tear, rupture or bulge the intervertebral space between two adjacent vertebras can decrease or displace abnormally and cause discomfort to the patient. When surgery is needed, the discs are replaced with implants that will heal or "fuse" the spine together. This device, with its associated stabilization, maintains the vertebral position while healing takes place. The result is referred to as "spinal fusion". The objective of spinal implants is to facilitate or maintain realignment and/or fixation of spinal elements. Clinical studies have demonstrated that surgeries using spinal implants are more effective at maintaining alignment and providing rigidity to the spine than surgeries in which implants are not used. Since the introduction of stabilizers as crude plates, rods, and wires, these devices have been developed into sophisticated appliances, which can be assembled and configured to rigidize spines of any size or condition. These stabilizers also provide mechanical fixation for restraint of an implanted graft material. With this fixation, displacement during healing is significantly reduced thereby reducing the failure rate. Failure of the stabilizer commonly results from screw breakage.

The majority of existing cervical stabilizers use plates that are bent in both the radial plain to conform to the vertebrae, and along the spinal axes to maintain lordosis. Bicortical screw purchase has been favored because of the increased strength of the construct and increased screw thread area within the bone. These screws are more technically challenging to place and add increased risk of morbidity from neural canal penetration and screw backout. The reduced bending reaction strength and decreased thread area of a unicortical screw purchase increases the probability of screw back out or loosening resulting in esophageal injury. Unicortical purchase results in a single point fixed end cantilever construct versus bicortical purchase which results in a dual point fixed end construct. Screw back out and loosening has led to the development of mechanisms for locking the screw head to the plate in unicortical screw plate designs. Such locking mechanisms not only prevent screw back out, they also reduce the tendency of the screw head to pivot within the plate. Locking the screw to a plate, rod or other insert results in a fixed point of attachment.

A second point of fixation results from the screw portion fixed within the bone. This produces a stress raiser of greatest stress, just below the screw attachment at the plate, rod or other implant. This is the area of most frequent screw breakage observed in clinical practice and biomechanical testing. This area of screw breakage is well known to those practiced in the art. In the lumbar spine, posterior screws break between the second and third thread below the plate or rod. In the cervical spine the anterior screws break at a similar location. In the present invention, particular embodiments are described below, These embodiments improve screw strength and lock the screw within the bone by extending a tapered unthreaded section of the screw shank into the bone.

SUMMARY OF THE INVENTION

A device and a method for stabilizing spinal vertebrae in a human spine for the purpose of temporarily fixing the vertebra with respect to other vertebrae, a graft, and with respect to other parts of the spinal column. The plate most commonly has a plurality of holes. The bone screw has a threaded portion that engages a predrilled or threaded hole in the vertebra or the graft. The bone screw also has a non-threaded portion that extends through the fixation plate, into the vertebrae, when the screw is seated. The bone screw maintains the plate in contact with the vertebra. The bone screw non-threaded portion is pulled into a locking mechanism on the plate. In the preferred embodiment the screw's non-threaded portion consists of a taper which locks into a stabilizing plate. The locking mechanism of the plate consists of a matching taper into which the screw shank is seated, locking the screw to the plate by an interference fit. The tapered or interference fit portion of the screw extends through the plate into the vertebral bone and is described as an extended shank.

BRIEF DESCRIPTION OF THE DRAWINGS

The present invention will be understood better from the following detailed description of the preferred embodiment. In the accompanying drawings the reference numbers refer to the individual parts described in the text.

FIG. 3 is a front (proximal) view of the spinal stabilization system shown implanted on the cervical portion of a human spinal column FIG. 4 is a front (proximal) view of the spinal stabilization plate.

FIG. 5 is an end sectional view, at 5—5 of FIG. 3, of the spinal stabilization system shown with a screw in the left side with the vertebrae removed. The drill/tap bushing is shown in the right side hole.

FIG. 6 is a side view of the spinal stabilization system screw.

DETAILED DESCRIPTION OF THE INVENTION

For simplification the stabilizer system is described as a single level cervical stabilizer in one of many conceivable embodiments. That is not to imply that this is the only embodiment within which the stabilizing system can be configured. For consistency in this patent the word stabilizer or implant refers to the plate screw assembly or parts thereof, whereas the word graft refers to the material replacing the removed disc or vertebrae. This device comprises a plate and bone screws fabricated from metal, alloy, polymeric, plastic, biodegradable, bio-absorbable, human tissue, allograft, and autograft or composite material. The plate may be fabricated into a multilevel configuration.

The Device

Figure 1:
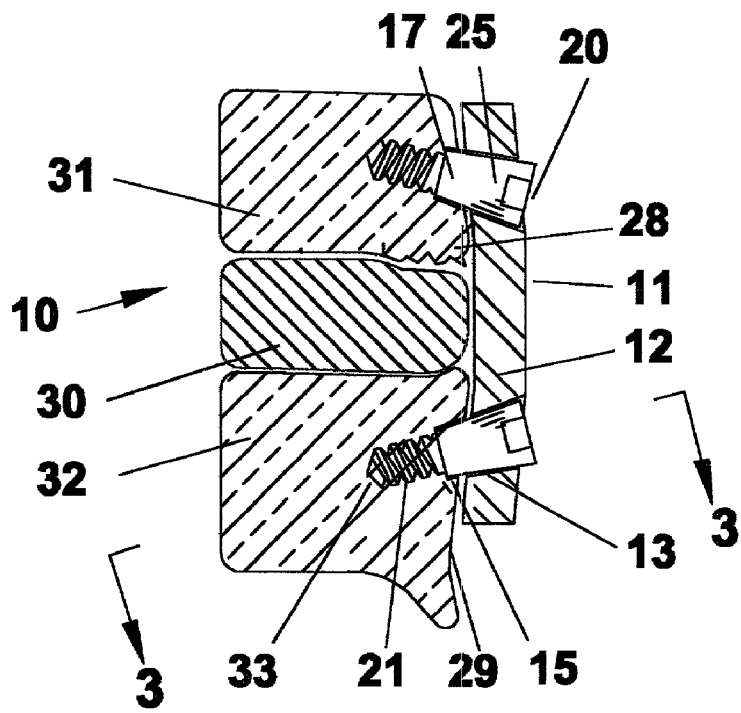
FIG. 1 is a side sectional view, at 1—1 of FIG. 3, of the spinal stabilization system shown implanted on the cervical portion of a human spinal column with the screws placed at an angle to the spinal column.
Figure 2:
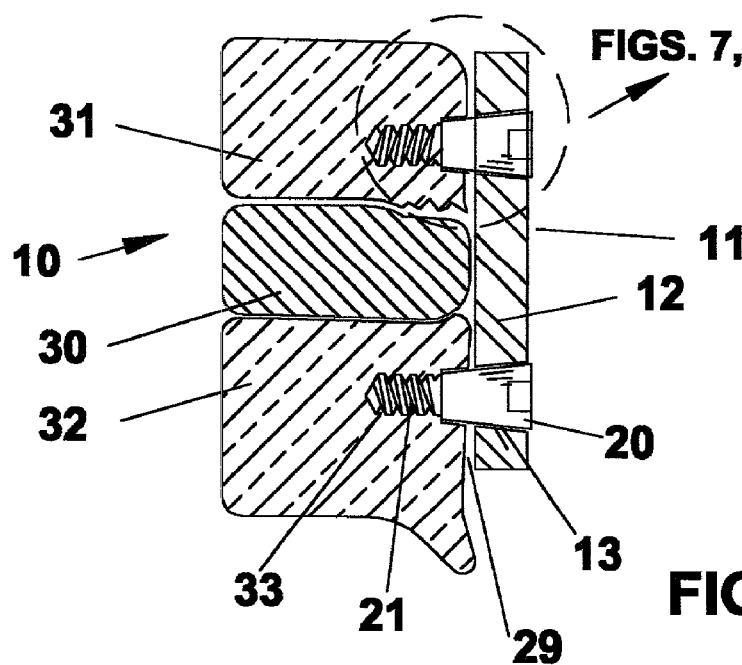
FIG. 2 is a side sectional view, at 2—2 of FIG. 3, of the spinal stabilization system shown implanted on the cervical portion of a human spinal column with the screws at 90 degrees to the spinal column.
Figure 7:
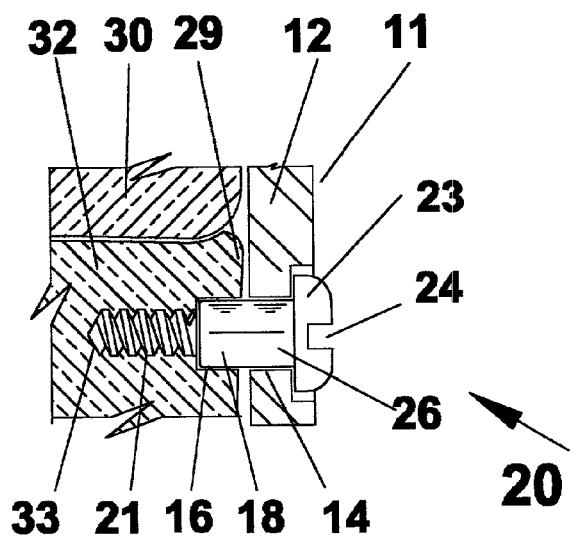
FIG. 7 is an enlarged sectional view, of the encircled area 7 of FIG. 2, with cylindrical bone and plate holes.
Figure 8:
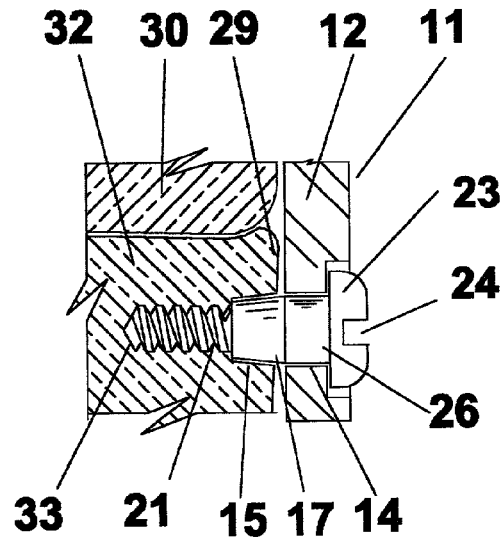
FIG. 8 is an enlarged sectional view of the encircled area 8 of FIG. 2. With the plate hole cylindrical and the bone hole tapered.
Figure 9:
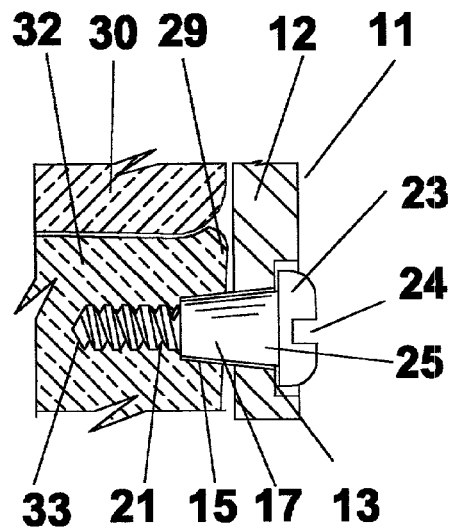
FIG. 9 is an enlarged sectional view of the encircled area 9 of FIG. 2. with the bone holes and plate holes tapered.
Figure 10:
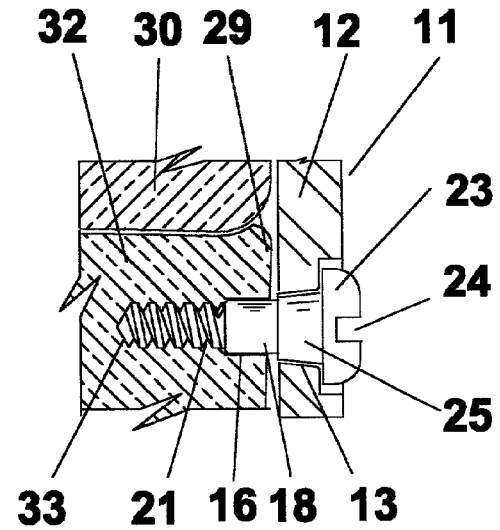
FIG. 10 is an enlarged sectional view of the encircled area 10 of FIG. 2. with bone holes cylindrical and plate holes tapered.

Referring to FIGS. 1, 2, and 3 in the preferred embodiment, the system is attached to the anterior surface of the spine 29. The system 10 may be modified for use on the lateral or posterior aspects of the spine. The system comprises plate 12 and bone screws 20. The system 10 and its components are described in detail in the following paragraphs. The bone stabilizing method of implanting is described in a subsequent section of this patent.

Referring to FIGS. 1, 2 and 3 in particular, the anterior cervical plate system 10 is shown in combination with bone screws 20. Each of the plate 12 tapered holes 13 receive a bone screw. Bone screws 20 each include a head 23, a threaded portion of the shank 21 and a tapered shank portion 25, between the head 23 and the threads. The tapered section has a minor diameter that equals or exceeds the major diameter of the threads of shank 21. These diameters allow the bone screws 20 to be inserted, shank first, into any of the screw holes 13 from the anterior side 11 of plate 12, with the threaded shank 21 passing through the hole 13 of the posterior surface. The thread engages a predrilled and pre-threaded hole 33 in the vertebra or the graft 30. The bone screw maintains the plate 12 in contact with the vertebrae 31 and 32. The screw's tapered portion 25 is pulled into the matching tapered hole 13 locking the screw 20 to the plate 12. The taper is configured to be self-locking preventing the screw from backing out. The taper is of sufficient length to extend into the vertebral bone. The taper will compress the bone hole resulting in increased strength of the bone-screw interface. The screws may be fixed to the plate and bone holes with adhesive, cement, or other bonding materials.

The Plate

The plate 12 is the framework upon which the bone screws 20 are attached. The plate 12 has two holes per vertebra, approximately perpendicular to the patient's spinal axis to receive and contain the bone screws 20. These screw holes may be angled to increase the preload as shown in FIG. 1 or installed with no angle as shown in FIG. 2. The plate has one hole for each screw tapered 13 or cylindrical 14. In the preferred embodiment the plate 12 is fabricated from a single piece of material. In prior art these plates contained threads for locking the screw or small locking devices such as cams were used to prevent the screws from backing out under sustained movement of the patient. To eliminate the use of plate threads on these materials the screw 20 is held in place with a taper 13 or a interference cylindrical fit 14 in the plate. The taper allows the use of the full thickness of the plate for a holding area. The plate may also be made in two or more levels.

The Bone Screw

In the preferred embodiment the bone screw, may use cylindrical or tapered bone screw threads 21, in the bone 31 and 32. As shown in FIGS. 7, 8, 9, and 10, the bone screw also has a section 22, tapered 17, or cylindrical 18, at the unthreaded portion of the shank, which engages the bone holes 15 or 16. The screw also has a tapered section 25 or a cylindrical section 26 which engages the plate holes 13 or 14. The screw has a feature 24 that will accept a driving tool. The driving feature may be incorporated into the section within the portion of the screw, which engages the plate so as not to protrude into the esophagus. A bone screw 20 is threaded into a drilled and tapped hole in a selected vertebra 31 and 32 to fix it into position. The tapered shank portion 22 extends into the vertebral bone, compressing the bone hole 15 or 16. The screw threaded distal portion passes through the plate. The screw may be self-tapping obviating the need for screw hole tapping. An alternate bone screw may have cylindrical shanks 18 or 26 with interference fits within the bone hole or the plate hole.

The Graft

After removing the disc and the cartilage, a graft 30, shown in FIGS. 1 and 2, preferably a non-degrading bone growth-compatible material is positioned between the two vertebrae 31 and 32 in the intervertebral space. Such grafts are structurally load-bearing devices, capable of withstanding the compressive forces supported by the adjacent superior vertebra 31, however they will not withstand the tensile force experienced at the vertebral to graft interface. The stabilizer 10 and the surrounding ligaments, tendons, and muscles must be preloaded to maintain compression between the graft 30 and the adjacent vertebra during any upper body motion that tends to put the vertebrae in tension. The graft 30 must be in compressive contact with the vertebral end plates 31 and 32. The graft 30 also may be metal, nonmetal, polymeric, allograft or autograft materials. A screw may be placed into the graft as well, with the tapered section extending into the graft material.

The Method

After the disc is removed the graft 30, as shown in FIGS. 1 and 2, is forced into position at the center of the vertebral end plates 31 and 32. Replacing damaged discs with rigid grafts is well known to those practiced in the art. The method of stabilizing the graft and maintaining the relationship between the two vertebrae is still a changing technology. The plate is selected and placed on the patient's vertebra 31 and 32. A portion of the vertebral protrusions 28 may be removed for a proper fit. The screws may be fixed to the plate and bone holes with adhesive, cement, or other bonding materials. The remainder of the method is presented as three procedures listed below.

The first procedure (1) utilizes plates 12 with pre-formed holes 13 or 14. In the second method (2) the plate contains no pre-formed holes. The plate holes are drilled or reamed into the plate at the time of placement in surgery. The third procedure (3) utilizes a template to guide the drilling and tapping operations. On frequently used plate sizes these templates may be used to align and position each drill and tap hole with respect to the other holes on the same plate. In all embodiments, the tapered thread shank screws may be self-tapping. Self-tapping screws are commonly used and are well known to those practiced in the art. Guide bushings and templates are used to align the drills and threading taps and to serve to protect the plate holes during drilling and tapping of the bone.

Procedure #1

Bushings 41are inserted into the pre-formed plate holes 13 or 14 to align the drill and thread tap and to protect the plate tapered hole. After inserting the bushings in the plate, the posterior side of the plate may be placed temporarily on the vertebra near the area where it will be attached and repositioned to determine the best location for the screws. The plate 12, with guide bushing 41 in place, as shown in FIG. 5, is used as a template to guide the drill and tap at the position and angle of the matching plate holes. Once the holes are threaded 33, and the guide bushings are removed, the screws 20 are partially threaded into these bone holes 15 or 16. The screws are then tightened to engage the plate locking mechanism and compress the extended tapered shank into the vertebral bone.

Procedure #2:

The tapered plate hole 13 or the cylindrical hole 14 and the bone holes 15 or 16, shown in FIGS. 7, 8, 9, and 10, may be drilled at the time of plate emplacement. In this procedure the plate 12 is positioned and then held using a positioning and/or holding means. This holding means fixes the plate in the preferred position for subsequent drilling and tapping operations. Once the plate 12 is positioned, the plate and the bone are drilled preferred position and direction through the plate and into the vertebrae 31 and 32 sequentially. A straight drill with a tapered section may be incorporated into one tool bit to facilitate taper placement. The holes are drilled through the plate and into the bone. In the preferred embodiment the taper is extended into the bone. The screw is then placed and tightened to engage the plate locking mechanism and to engage the extended tapered shank into the vertebral bone.

Procedure #3.

In this procedure cylindrical bone hole 16 or the tapered bone hole 15 and thread hole 33, shown in FIGS. 7, 8, 9, and 10, are drilled through a template that closely approximates the plate contour and hole placement. The drilling and threading operations are performed through the template thereby aligning with and protecting the existing holes 13 or 14 in the plate 12. When the drilling and threading operations are completed and the plate is permanently positioned and secured with the screws 20.

We claim:

1. A system for stabilizing a first bone segment within a bone column relative to a second bone segment in the bone column, the stabilizing system comprising:

a plurality of bone screws, each having a head portion at a first end thereof and a threaded shank portion at a second end thereof, with an unthreaded shank portion therebetween; and a rigidizing plate, with a plurality of tapered holes corresponding to the plurality of bone screws, each hole being sized and configured for making a locking fit with a first portion of the unthreaded shank portion of the bone screw received therein, the plate sized to position at least two holes for screw placement therethrough into the first bone segment and at least two holes for screw placement therethrough into the second bone segment;

wherein a second portion of the unthreaded shank portion passes through the plate hole and extends into the bone segment when the threaded shank portion is engaged into the bone segment.

2. The bone stabilizing system of claim 1, wherein the screws are fixed to the plate and the bone holes with an adhesive material.

3. The bone stabilizing system of claim 1, wherein the screws have self-tapping screw threads.

4. The stabilizing system of claim 1, wherein:

a radial shoulder delineates the head portion from the first unthreaded shank portion.

5. A bone stabilizing method, using plates with holes and bone screws for the purpose of fixing one bone segment with respect to one or more other bone segments or implants within a bone column comprising the following steps:

(a) providing the system components of claim 1;

(b) machining holes in the bone segments for the purpose of retaining the engagement of the bone screws and retaining fixation of the plate to the bones, and (c) placing the screws, with a shank portion and a head portion configured and sized to be affixed by an interference fit within the plate hole and the bone.

* * * * *